United States Patent
Preveraud et al.

(10) Patent No.: US 10,765,639 B2
(45) Date of Patent: Sep. 8, 2020

(54) NANOCAPSULES, METHODS OF MANUFACTURE AND USES THEREOF

(71) Applicant: ADISSEO FRANCE S.A.S., Antony (FR)

(72) Inventors: Damien Preveraud, Néris les Bains (FR); Véronique Rosilio, Paris (FR)

(73) Assignee: ADISSEO FRANCE S.A.S., Antony (FR)

( * ) Notice: Subject to any disclaimer, the term of this patent is extended or adjusted under 35 U.S.C. 154(b) by 0 days.

(21) Appl. No.: 16/088,242

(22) PCT Filed: Mar. 17, 2017

(86) PCT No.: PCT/FR2017/050622
§ 371 (c)(1),
(2) Date: Sep. 25, 2018

(87) PCT Pub. No.: WO2017/162963
PCT Pub. Date: Sep. 28, 2017

(65) Prior Publication Data
US 2019/0083414 A1    Mar. 21, 2019

(30) Foreign Application Priority Data
Mar. 25, 2016  (FR) .................................. 16 52592

(51) Int. Cl.

| | | |
|---|---|---|
| *A23K 20/158* | (2016.01) | |
| *A61K 9/51* | (2006.01) | |
| *A23K 40/30* | (2016.01) | |
| *A23K 10/30* | (2016.01) | |
| *A23K 20/174* | (2016.01) | |
| *A23K 50/75* | (2016.01) | |
| *A61K 31/355* | (2006.01) | |
| *A61K 31/122* | (2006.01) | |
| *A61K 31/07* | (2006.01) | |
| *A61K 9/50* | (2006.01) | |
| *A61K 31/593* | (2006.01) | |

(52) U.S. Cl.
CPC ............ *A61K 9/5192* (2013.01); *A23K 10/30* (2016.05); *A23K 20/158* (2016.05); *A23K 20/174* (2016.05); *A23K 40/30* (2016.05); *A23K 50/75* (2016.05); *A61K 9/5015* (2013.01); *A61K 9/5123* (2013.01); *A61K 9/5161* (2013.01); *A61K 31/07* (2013.01); *A61K 31/122* (2013.01); *A61K 31/355* (2013.01); *A61K 31/593* (2013.01)

(58) Field of Classification Search
None
See application file for complete search history.

(56) References Cited

U.S. PATENT DOCUMENTS

| | | | | |
|---|---|---|---|---|
| 8,877,217 | B2 * | 11/2014 | Kim ......................... | A61K 8/11 424/401 |
| 2003/0180369 | A1 * | 9/2003 | Grisoni .................... | A61K 8/11 424/490 |
| 2015/0231069 | A1 * | 8/2015 | Modi ................... | A61K 9/1075 424/455 |
| 2019/0000763 | A1 * | 1/2019 | Pilgaonkar ........... | A61K 9/5031 |

FOREIGN PATENT DOCUMENTS

| | | | |
|---|---|---|---|
| EP | 1018363 | A1 | 7/2000 |
| EP | 1552820 | * | 7/2005 |
| EP | 1552820 | A1 | 7/2005 |
| FR | 2803203 | A1 | 7/2001 |
| FR | 2924943 | A1 * | 6/2009 |
| WO | 2010040194 | A2 | 4/2010 |

OTHER PUBLICATIONS

Mora-Huertas, C. et al. Polymer Based Nanocapsules for Drug Delivery International J of Pharmaceutics 385:113-142, 2010. (Year: 2010).*
Desmarchelier C. et al. The Distribution and Relative Hydrolysis of Tocopheryl Acetate in the Different Matrices Coexisting in the Lumen . . . Molecular Nutrition & Food Research 57(7)1237-1245, Jul. 2013. (Year: 2013).*
Beck R. et al. Nanocosmetics and Nanomedicines Springer 2011. Chapter 3 Polymeric Nanocapsules: Concepts and Applications by Poletto et al. 49-68. (Year: 2011).*
Ogawa S. et al. Production and Characterization of O/W Emulsions Containing Droplets Stabilized by Lecithin-Chitosan-Pectin Multlayered Membranes J Agricultural and Food Chemistry 52:3595-3600, 2004. (Year: 2004).*
Ogawa S. et al. Influence of Environmental Conditions on the Stability of Oil in Water Emulsions Containing Droplets Stabilized by Lecithin-Chitosan Membranes J Agricultural Food Chem 51:5522-5527, 2003. (Year: 2003).*
International Search Report dated May 31, 2017 re: Application No. PCT/FR2017/050622, pp. 1-3, citing: EP 1 552 820 A1, FR 2 924 943 A1, EP 1 018 363 A1, FR 2 803 203 A1 and WO 2010/040194 A2.

* cited by examiner

*Primary Examiner* — Ralph J Gitomer
(74) *Attorney, Agent, or Firm* — Cantor Colburn LLP

(57) ABSTRACT

The invention concerns nanocapsules in the form of a colloidal suspension or in dry form, said nanocapsules comprising at least an active ingredient in the form of an oil, one ionic surfactant, optionally one nonionic surfactant, and one hydrophilic polymer. The invention also concerns their manufacture and their uses.

14 Claims, 4 Drawing Sheets

NANOCAPSULES, METHODS OF MANUFACTURE AND USES THEREOF

TECHNICAL FIELD

The disclosure concerns nanocapsules of fat-soluble active ingredients, their manufacturing method and their uses.

BACKGROUND

Molecules, such as vitamins, fatty acids, essential oils, are very widely used in many technical fields such as the pharmaceutical, cosmetic and agri-food industries, and in particular in the animal nutrition field. As an example, vitamins A and E are commonly used for the preparation of feed promoting animal growth and health.

Their hydrophobic nature and their environmental, in particular thermal and chemical fragility, during their formulation and storage, as well as during their use, make their encapsulation necessary.

The vitamin E, or tocopherol (in abbreviated form, TOL), existing predominantly in the form of α-tocopherol (αTOL), is, in the native state, an oily, lipophilic, miscible liquid in all proportions in any hydrophobic or lipid phase. It is extremely unstable, easily oxidizable and, in the oxidized state, it loses most of its biological activity. Its bioavailability in animals does not exceed 50% when it is orally administered, since, rapidly oxidized, it is mainly absorbed in this oxidized, inactive form. Also, when it is orally administered, vitamin E is in the form of a more stable derivative, generally selected from esters, for example acetate, and vitamin E salts.

The vitamin A exists in several forms, in particular as an ester, and it is in one of its most stable forms, the retinyl acetate form, that it is most often consumed by livestock animals (poultry, pigs and cattle). However, it remains sensitive to oxidation, temperature, light, acids. In pharmaceutical application or animal nutrition, it is thus very rapidly degraded as soon as it meets the first severe conditions, in particular acidic conditions, of the digestive system, which does not make it a bioavailable form of the vitamin A.

In order to best preserve these sensitive active ingredients, it is known for long that they can be protected by coating or encapsulation. Various means for encapsulating vitamins in particular A and E have been developed and widely used, such as means involving proteins.

BRIEF SUMMARY

We are, however, still looking for a formulation of a fat-soluble active ingredient that would be highly bioavailable.

The authors have been looking for a new formulation of such active ingredients that is capable of increasing their absorption in particular their intestinal absorption.

Since most of these active ingredients is generally used in their protected form, it was further essential to develop a formulation that allows said active ingredients to be absorbed in their free, active form, which means that the hydrolysis of the protected form and the absorption must occur almost simultaneously.

The authors first discovered that such active ingredients could be formulated into nanocapsules with a high content of said active ingredients, and this thanks to a clean method, in the meaning that it does not use any organic solvent. Then, the authors have developed nanocapsules capable of releasing, in an efficient manner, the active form of the active ingredient, namely, in a form satisfying all the requirements above.

Thus, the disclosure concerns a formulation of fat-soluble active ingredient(s) in a high content, in the form of nanocapsules, which, in a preferred variant, has a bioavailability higher than the formulations of the current market.

The disclosure further aims at implementing an industrializable and environment-friendly manufacturing method, for obtaining such nanocapsules. In addition, the method developed by the authors leads to nanocapsules having a low residual moisture, preferably less than 8%, which gives them stability over time, regardless of the storage conditions.

According on the field of application of the active ingredient, the nanocapsules of the disclosure may be put into a form for easier handling, for example in the form of microparticles, in particular by adsorption of said nanocapsules on a support. In the following description, the term "particle" will be reserved for any presentation of said nanocapsules, and by way of example, such particles are microparticles comprising nanocapsules of the disclosure. If the active ingredient is intended for animal nutrition, it is thus particularly advantageous that the nanocapsules are formulated into dry particles having an excellent mixability for their incorporation into a premix. In this indication, such particles are microparticles having an average size less than 300 μm.

The disclosure is hereinafter more specifically described with reference to vitamin E, but obviously, its scope is not restricted thereto, and it applies to any fat-soluble active ingredient and any mixture of such substances.

As previously said, the disclosure relates to nanocapsules comprising at least an fat-soluble active ingredient, in a high concentration, that are stable and that can be highly bioavailable. The nanocapsules of the disclosure may be in the form of a colloidal suspension, or in dry form, after drying of this suspension.

Whether in the form of a colloidal suspension, or in dry form, said nanocapsules comprise at least an oily fraction comprising a fat-soluble active ingredient and an ionic surfactant, and one preferably hydrophilic polymer surrounding said oily fraction.

The authors unexpectedly discovered that, order to make vitamin E bioavailable, or at the very least increase its bioavailability, the nanocapsules must further comprise at least a nonionic surfactant. Of course, depending on the indications of the active ingredient, this bioavailability may not be desired or even proscribed, then the nanocapsules will be devoid of such a nonionic surfactant.

As already mentioned, the nanocapsules of the disclosure allow to convey any fat-soluble active ingredient. Thus, the latter can be selected from:

fat-soluble vitamins such as vitamins A, D, E, K, their derivatives, in particular esters, for example acetate, propionate or succinate, as well as their metabolites such as retinal, retinoic acid, 25-hydroxycholecalciferol, 1,25 dihydroxycholecalciferol;

carotenoids;

essential oils such as thyme, oregano, rosemary, garlic, camellia, mustard, ginger, turmeric, grape, citrus fruits, sainfoin, yucca, mugwort, cinnamon, mint, clove, berries, cumin and Echinacea essential oils;

saturated, monounsaturated and polyunsaturated fatty acids; fatty oils.

If the active ingredient is liquid or likely to be liquid by heating, it may constitute on its own the oily phase in which the ionic surfactant will be present.

If it is not in the liquid state at the manufacturing temperature of the nanocapsules, it can be solubilized beforehand in an oil, generally inert oil, which will be used as a support. As an example, this oil may be triolein.

An interest of the nanocapsules of the disclosure lies in their active ingredient content which can range from a minimum of for example 5% by mass relative to the dry mass of the nanocapsules (m/m), to more than 50%, or even at least 90%. This content will be determined depending on the destination of the nanocapsules, it is generally at least 5% by mass relative to the dry mass of the nanocapsules (m/m), preferably at least 25%, and more preferably at least 50%, or even at least 70%, even at least 90%.

Said ionic surfactant is preferably selected from those whose molecular weight is of at most 1500 g/mol, or even at most 1000 g/mol. Above 1500 g/mol, the nanocapsules are hardly formed. From these preferred surfactants, phosphatidylcholines can be retained, such as egg lecithin or soy lecithin, or hexadecyltrimethylammonium bromide. The ionic surfactant, positively or negatively charged, is selected to be of a charge opposite to that of the polymer.

Said nonionic surfactant is preferably selected from polyoxyethylene-polyoxypropylene block copolymers, blends of polyoxyethylene (EO)-polyoxypropylene (PO) block copolymers, Tween 80, fatty acids and sucrose esters and in particular palmitates and stearates, and any mixture thereof. Within the framework of this definition, the preferred surfactants are selected from copolymers of formula $EO_x$—$PO_y$-$EO_x$ wherein x ranges from 75 to 85 and y ranges from 25 to 35, copolymers of formula $EO_x$—$PO_y$-$EO_x$ wherein x ranges from 55 to 65 and y ranges from 35 to 45 and copolymers of formula $EO_x$—$PO_y$-$EO_x$ wherein x ranges from 112 to 123 and y ranges from 40 to 50, as well as fatty acids and sucrose esters marketed under the brands SISTERNA® SP70 and PS750.

The polymer(s) allowing to obtain nanocapsules according to the disclosure are selected from cationic or anionic polymers, the charge of the polymer being opposite to that of the ionic surfactant. It is preferably of natural origin, thus, one or more polymer(s) selected from chitosan, alginate, pectin, starch, cellulose, casein and combinations thereof, will be preferably retained. Thus, the preferred polymer-ionic surfactant combinations are those constituted by chitosan and egg lecithin, and alginate and CTAB.

According to a preferred variant of the disclosure, the content of the nonionic surfactant as defined above, in the suspension, is of at least 15% by mass relative to the dry mass of the nanocapsules (m/m).

The disclosure further provides nanocapsules resulting from the drying of the colloidal suspension described above. These nanocapsules therefore comprise at least an oily fraction comprising a fat-soluble active ingredient, an ionic surfactant, optionally a nonionic surfactant, and a polymer preferably hydrophilic polymer, said nanocapsules being obtainable by drying a colloidal suspension of the disclosure. Drying is advantageously carried out in the presence of lactose, the nanocapsules of the disclosure being adsorbed on lactose.

The disclosure also provides particles comprising nanocapsules as described above, said nanocapsules being adsorbed on a support. This support may be selected from any inert support, such as for example the lactose. In a preferred variant, these particles are microparticles comprising nanocapsules of the disclosure adsorbed on lactose.

A method of the disclosure for manufacturing nanocapsules, whether they are in a colloidal suspension above or in the dry state after treatment of such suspension.

Thus, a method for manufacturing a colloidal suspension of nanocapsules comprises the following steps:

There is, on the other hand, a first phase comprising at least an oily fraction comprising at least a fat-soluble active ingredient and an ionic surfactant and, on the one hand, a second aqueous phase comprising at least a polymer and optionally a nonionic surfactant, the molar concentration of said ionic surfactant and the one of the nonionic surfactant, if appropriate, being greater than or equal to 100 times the critical micelle concentration (CMC) of said ionic surfactant(s) and said nonionic surfactant(s), respectively; the active ingredient(s), ionic surfactants, nonionic surfactants and polymers meeting the definitions given above;

A coarse emulsion is formed which is afterwards homogenized under high pressure to form the colloidal suspension of nanocapsules.

The determination of the CMC can be done by any technique well known to the one skilled in the art, for example by measurements of surface tension by a blade or a ring tensiometer.

If the active ingredient(s) is/are not liquid at room temperature or is/are too viscous, the oily and aqueous phases are brought to a temperature ranging from 60 to 70° C., allowing the melting of the active ingredient(s).

The emulsion called coarse emulsion is obtained by simple stirring of the aqueous and oily phases. Its homogenization is afterwards carried out under high pressure, for example for at least 6 minutes, at a pressure preferably at least equal to 600 bars.

In order to obtain dry nanocapsules according to the disclosure from a colloidal suspension of nanocapsules as described above, said nanocapsules are spray-dried in the presence of lactose. This method leads to particles that are non-tacky and that can be stored at room temperature.

The disclosure also concerns the uses of such nanocapsules. They are of great interest in animal nutrition, in particular for monogastric animals. In this indication, they are used in the form of particles, and in particular in the form of microparticles, as described above.

BRIEF DESCRIPTION OF THE DRAWINGS

The disclosure is illustrated and its advantages highlighted in the following examples exposing the manufacture of alpha-tocopherol acetate nanocapsules (αTAC) and their performances in animal nutrition in in vitro and in vivo assays.

DETAILED DESCRIPTION; EXAMPLES

Figure 1:
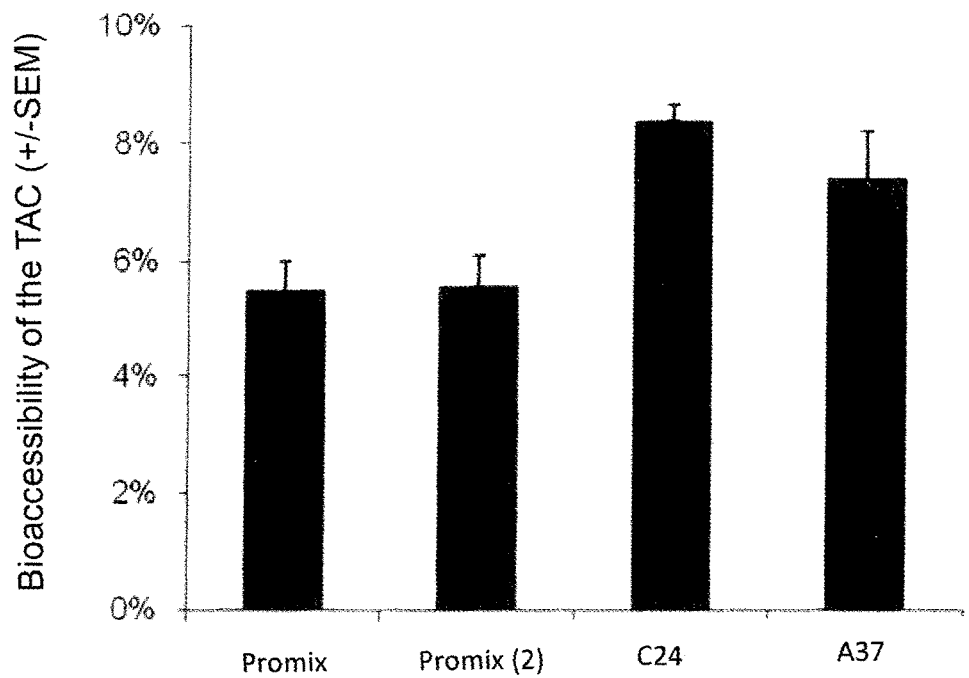
FIG. 1 shows the in vitro bioaccessibility rate of TAC of different TAC formulations.

In the following examples, various parameters are analyzed and particularly the vitamin E bioavailability.

The bioavailability of a fat-soluble active ingredient, such as vitamin E, or a vitamin E derivative is represented by the concentration of vitamin E released into the blood, relative to the concentration of vitamin E present in the ration of the animal, or relative to the concentration expressed as equivalent of vitamin E of the vitamin E derivative introduced into the ration of the animal, when a vitamin derivative is administered. This representation of the bioavailability of vitamin E therefore takes into account the absorption of vitamin E or the derivative of vitamin E in the intestine during the digestive transit.

EXAMPLE 1

Manufacturing of Nanocapsules According to the Disclosure

Formulation

The nanocapsules prepared in this example are identified by the references C24, A37 and C40.

They are obtained from a colloidal suspension comprising at least:

TAC an ionic surfactant selected from egg lecithin (Lipoid E80) and hexadecyl trimethylammonium bromide (CTAB), for the nanocapsules C24 and A37, a nonionic surfactant Lutrol®-F68, at least a ionic hydrophilic polymer selected from (cationic) chitosan and (anionic) sodium alginate, said colloidal suspension being afterwards dried in the presence of lactose.

The formulation of these nanoparticles is shown in the following table 1, the content of the ingredients being expressed in % (m/m of dry matter):

TABLE 1

|  |  | Particles | | |
| --- | --- | --- | --- | --- |
|  |  | C24 | A37 | C40 |
| Active ingredient | TAC | 24 | 37 | 39 |
| Ionic surfactant | Lipoid E80 | 12 | — | 10 |
|  | CTAB | — | 4.5 | — |
| Nonionic surfactant | Lutrol ®-F68 | 15 | 23 | — |
| Polymer | Chitosan | 13 | — | 10 |
|  | Sodium alginate | — | 8.1 | — |
| Support | Lactose | 36 | 27.4 | 41 |

Manufacture

The method for manufacturing nanoparticles has the 3 following steps:

preparing the nanoemulsion, preparing the colloidal suspension of nanocapsules, and drying the nanocapsules.

Protocol for Manufacturing the Nanocapsules C24 and A37:

Preparing the nanoemulsion:

For the nanocapsules C24:

the ionic surfactant, Lipoid E80, is dispersed in the TAC, under stirring with a turbine, and the dispersion is brought to 65° C., in order to obtain an oily phase, the nonionic surfactant (Lutrol® F68) is dissolved in water and the solution is brought to 65° C., in order to obtain an aqueous phase, For the nanocapsules A37:

the TAC, which constitutes the oily phase, is brought to 65° C., and the ionic surfactant, CTAB, is dispersed therein, the nonionic surfactant (Lutrol® F68) is dissolved in water and the solution is brought to 65° C., in order to obtain an aqueous phase, then for the nanocapsules C24 and A37:

the aqueous phase is added to the oily phase under stirring and a primary or coarse emulsion is formed using a Reyneri turbine at 600 tours/min, at 65° C., for 15 minutes, the emulsion is transferred into the high-pressure homogenizer and homogenized at a pressure of 600 bars for 6 minutes at 65° C., in order to obtain the nanoemulsion.

Preparing of the colloidal suspension of the nanocapsules:

the nanoemulsion obtained above is $\frac{1}{10}^{th}$ diluted with a solution of Lutrol® F68, the chitosan acetic solution is added at 0.05 g/L for the nanocapsules C24 or the sodium alginate solution is added at 1.8 g/L for the nanocapsules A37, under the turbine and stirred for 2 hours at room temperature, in order to obtain a colloidal suspension of nanocapsules, according to the disclosure.

Drying of the nanocapsules:

the nanocapsules are spray-dried on lactose; the parameters are a 15% pump flow rate, a 150° C. inlet temperature, a 7 mL/min flow rate and a 500 L/h compressed air flow.

Protocol for Manufacturing the Nanocapsules C40:

The nanocapsules C40 are manufactured according to the method described above for the nanocapsules C24, except that no nonionic surfactant is added.

Characterization of the Nanocapsules:

The nanocapsules are characterized by their size indicated in the following Table 2, at two stages of the manufacturing method, the first at the formation of the nanoemulsion, before the addition of the polymer and the second at the end of the method before drying the nanocapsules:

TABLE 2

|  | Nanoparticles | | |
| --- | --- | --- | --- |
|  | C24 | A37 | C40 |
| Size of the nanodroplets, before addition of the polymer (nm) | 219 | 236 | 123 |
| Nanocapsule size before drying (nm) | 355 | 342 | 163 |

The following examples illustrate the interest of the TAC formulations according to the disclosure by assessing the bioavailability of the TAC.

The bioavailability of the TAC of a formulation corresponds to the proportion of TOL absorbed by the intestinal mucosa that will be used for the cell metabolism and the organ functions. This bioavailability is the combination of different factors, and in particular the bioaccessibility of the TAC, that is to say the proportion of vitamin E present in a formulation (in the form of TAC) which is solubilized in the mixed micelles, and the hydrolysis of TAC in TOL by the carboxy ester hydrolase (CEH) secreted in the digestive system.

EXAMPLE 2

Bioaccessibility of TAC in TAC Formulations Assessed in In Vitro Assays

This test is described by Desmarchelier et al., 2013. Mol. Nutr. Food Res. 2013, 57, 1237-1245.

In these in vitro assays, mixed micelles containing different TAC formulations of Example 1 are prepared, which allow reproducing the conditions of digestion by imitating the micelles involved in the intestine.

The bioaccessibility of vitamin E is calculated after in vitro digestion of the feed containing the different formulations. It is determined by the ratio between vitamin E measured out by HPLC found in the micellar phase, and vitamin E measured out by HPLC present in the digestate obtained at the end of the duodenal phase.

The assays are carried out on three types of formulation:
  the nanocapsules C24 and A37 of example 1: the nanocapsules A37 are tested in two forms: a powder form with lactose supporting (A37); and
  a product identified by the reference Promix, comprising a vitamin E oil adsorbed on silica (Promix and Promix (2) are two repetitions of the same product)

The results are shown in FIG. 1.

It is observed that the nanocapsules of TAC (C24 and A37) allow increasing the bioaccessibility of vitamin E relative to the Promix product, that is to say, the amount of vitamin E contained in the food matrix that is solubilized in the mixed micelles at the end of an in vitro digestion.

EXAMPLE 3

Hydrolysis of TAC in TOL by CEH in In Vitro Assays

The protocol of hydrolysis of the vitamin E-acetate (TAC) by CEH is described by Desmarchelier et al., 2013. Mol. Nutr. Food Res. 2013, 57, 1237-1245.

Briefly, 500 µl of mixed micelles containing the TAC are incubated for 30 minutes at 37° C. CEH is afterwards added at a concentration of 10 U/mL for 30 min. The appearance of free tocopherol (TOL) is then measured by HPLC.

The assays are carried out on three types of formulation:
  the nanocapsules C24 and A37 of the example 1; and
  a product identified by the reference E Promix, comprising a vitamin E oil.

Figure 2:
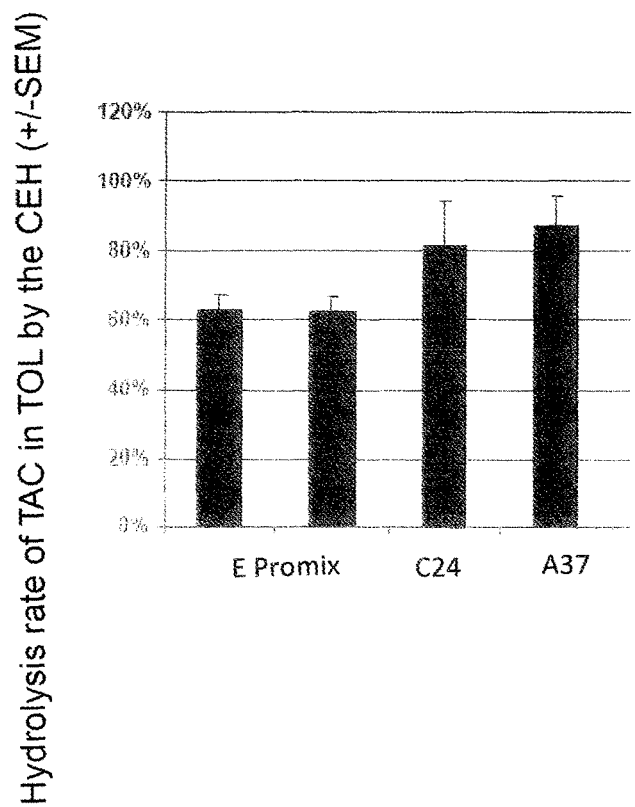
FIG. 2 shows the in vitro hydrolysis rate of TAC in TOL of different TAC formulations.

The results are shown in FIG. 2.

The TAC nanocapsules (C24 and A37) allowing to increase the conversion of TAC into TOL relative to the E Promix product, resulting in a larger amount of vitamin E available for absorption.

EXAMPLE 4

Bioavailability of TAC in In Vivo Assays in Rats

Protocol

The assays are carried out on 6-week-old male Wistar rats fed for 2 weeks with a tocopherol-deficient feed.

The rats were fasted the night before the force-feeding.

The rats (n=10) were force-fed for 5 consecutive days with 5 mg of different TAC solutions in water:
  Microvit® E Promix 50 (vitamin E acetate adsorbed on silica),
  C24 dry nanocapsules of example 1, and
  Dry nanocapsules A37 of example 1.

Three hours after the last force-feeding, the rats were anesthetized, blood was collected by intracardiac puncture and, after centrifugation, the plasma was isolated. After a double hexanic extraction, the plasma concentration of alpha-tocopherol ($\alpha$TOL) was measured by HPLC.

Results

Figure 3:
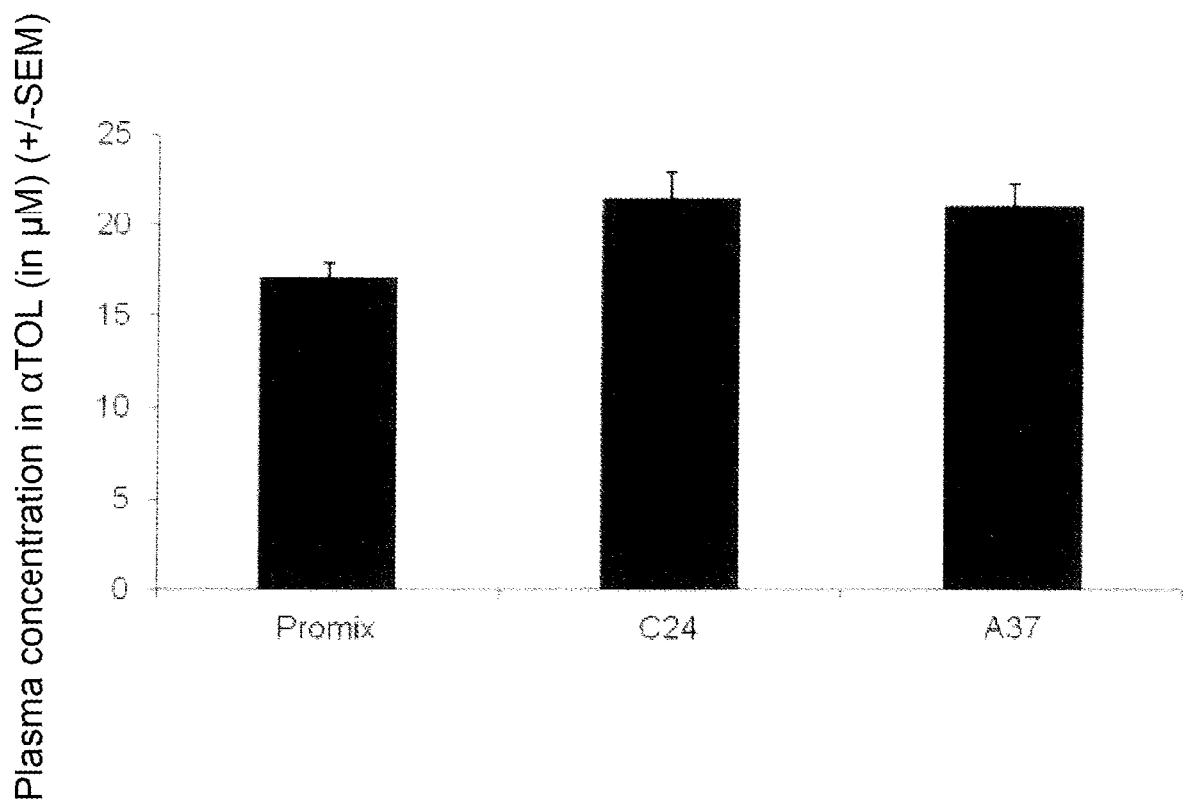
FIG. 3 shows the plasma αTOL concentration (in μM) in rats after force-feeding administration of different TAC formulations.

The results are reported in FIG. 3.

The force-feeding with the formulations C24 and A37 has led to plasma concentrations in $\alpha$TOL, respectively 26% and 24%, significantly higher (P<0.001) than the force-feeding with the Microvit® E Promix 50.

EXAMPLE 5

Bioavailability of TAC in In Vivo Assays In Roosters

Protocol

The experimental scheme is described in detail in Preveraud et al. 2015, British Poultry Science, 56: 1; 94-102.

Briefly, two rooms with 60 ISA Brown roosters are placed in individual cages. One week before assigning the treatments, the roosters are fed with a feed devoid of vitamin E.

The roosters (n=10 roosters per treatment) were force-fed with different TAC solutions in water.
  Room 1: Dry nanocapsules C24 of example 1,
  TOL and TAC, in the form of oil, as a blank
  Room 2: C40 dry nanocapsules of example 1,
  TOL and TAC, in the form of oil, as a blank.

After the force-feeding administration of the vitamin E products put in a capsule, blood samples were taken at 0, 6, 12, 24, 48 and 96 h post force-feeding. After centrifugation, the plasma is decanted and the free tocopherol is measured up by HPLC.

Results

Figure 4:
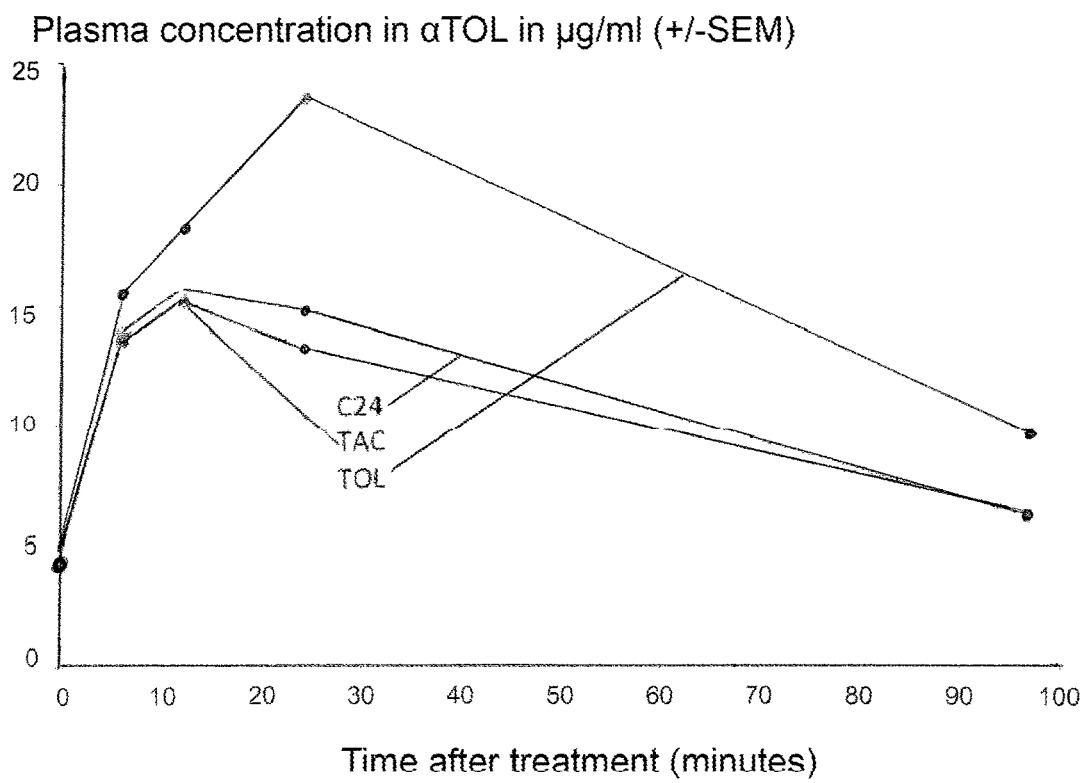
FIGS. 4 and 5 show the plasma αTOL concentration (in μg/ml) in roosters after force-feeding administration of different TAC formulations.
Figure 5:
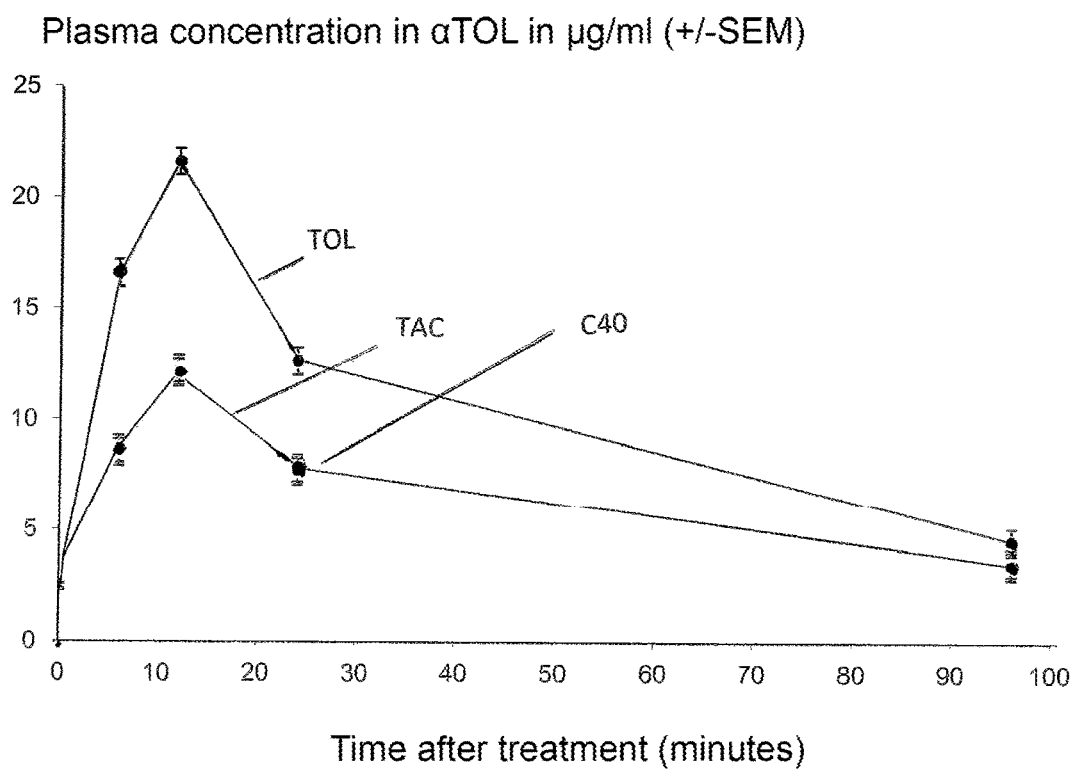

The results are illustrated in FIGS. 4 and 5 and reported for the 24 h and 96 h times in the following tables 3 and 4, wherein the diffusion of vitamin E in the blood is expressed by the area under the curve (AUC) and the diffusion percentage relative to the TAC.

TABLE 3

| Vit E (Room 1) | 24 h | | 96 h | |
|---|---|---|---|---|
| | AUC µg/ml/h | %/TAC | AUC µg/ml/h | %/TAC |
| TAC | 206 | — | 597 | — |
| TOL | 307 | +49% | 1193 | +100% |
| C24 | 228 | +11% | 690 | +16% |

The force-feeding with the formulation C24 has led to plasma $\alpha$TOL concentrations significantly higher than the force-feeding with the unformulated TAC.

TABLE 4

| Vit E (Room 2) | 24 h | | 96 h | |
|---|---|---|---|---|
| | AUC µg/ml/h | %/TAC | AUC µg/ml/h | %/TAC |
| TAC | 142 | — | 340 | — |
| TOL | 309 | +118% | 320 | +124% |
| C40 | 146 | +3% | 719 | +6% |

The force-feeding with the formulation C40 has led to plasma $\alpha$TOL concentrations which are not significantly different from those of the unformulated TAC control, and prepared in the absence of a nonionic surfactant, therefore, it has no bioavailability potential.

EXAMPLE 6

Bioavailability of TAC in In Vivo Assays in Chickens

Protocol 1-day-old chickens fed for 7 days with a tocopherol-deficient feed are being studied; the total duration of the experimental phase is fixed at 15 days during which they receive different treatments of vitamin E mixed with the granulated feed (n=18 per treatment). Beforehand, chickens were placed in groups of 6 per cage. At the age of 21 days, the animals are euthanized and liver samples were taken. After extraction, the vitamin E is measured up in this tissue.

The chickens were fed by the following formulations:
Microvit® E Promix 50, E50 (vitamin E acetate adsorbed on silica),
Dry nanocapsules C24 of example 1.

After the force-feeding administration of the vitamin E products put in a capsule, blood samples were taken at 0, 6, 12, 24, 48 and 96 h post force-feeding. After centrifugation, the plasma is decanted and the free tocopherol is measured up by HPLC.

Results

Figure 6:
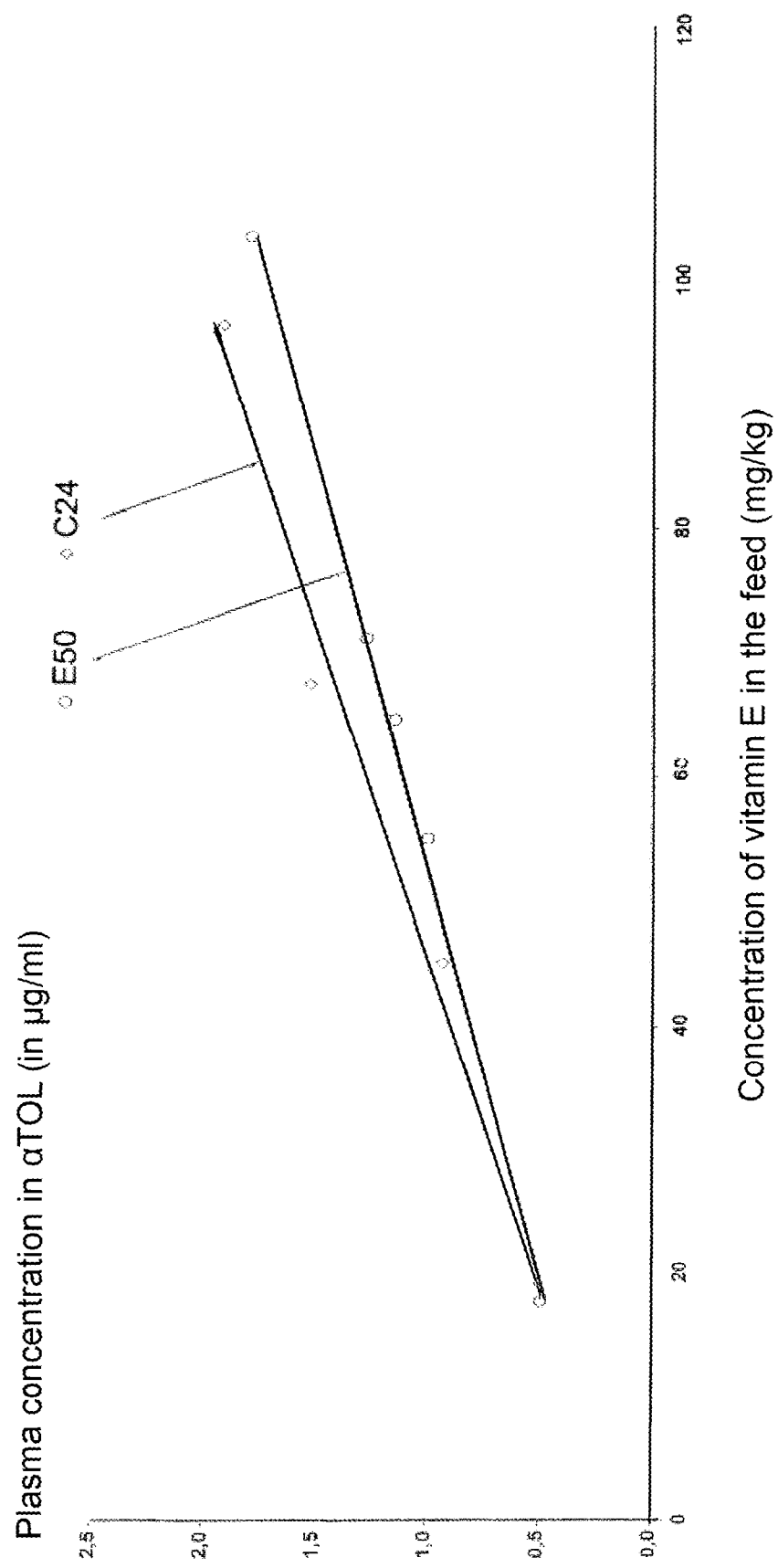
FIG. 6 shows the plasma αTOL concentration (in μg/ml) in chicken after administration, in the feed, of different TAC formulations.

The results are reported in FIG. 6.

The force-feeding with the formulation C24 has led to plasma αTOL concentrations significantly higher than force-feeding with the E50 product.

The force-feeding feed with the C24 formulation has led to hepatic αTOL concentrations (+24%) significantly higher than the diet with the formulation E50 based on the comparison of the right slopes of the dose-response effect.

The invention claimed is:

1. Nanocapsules comprising an oily fraction comprising an active ingredient in the form of an oil, an ionic surfactant, a nonionic surfactant, and a hydrophilic polymer surrounding said oily fraction, wherein said ionic surfactant and said hydrophilic polymer have opposite charges.

2. The nanocapsules according to claim 1, wherein said active ingredient comprises at least one of vitamin A, vitamin D, vitamin E, vitamin K and their derivatives and their metabolites, essential oils, fatty acids, fatty oils and any mixtures thereof.

3. The nanocapsules according to claim 2, wherein said active ingredient comprises an essential oil of at least one of thyme, oregano, rosemary, garlic, camellia, mustard, ginger, turmeric, grape, citrus fruits, sainfoin, yucca, mugwort, cinnamon, mint, clove, berries, cumin and Echinacea.

4. The nanocapsules according to claim 1, wherein said ionic surfactant has a molecular weight of at most 1500 g/mol.

5. The nanocapsules according to claim 1, wherein the ionic surfactant comprises at least one of phosphatidylcholines and hexadecyltrimethylammonium bromide.

6. The nanocapsules according to claim 1, wherein said nonionic surfactant comprises at least one of polyoxyethylene-polyoxypropylene block copolymers, blends of polyoxyethylene (EO)-polyoxypropylene (PO) block copolymer, Tween 80, fatty acids and sucrose esters, and any mixture thereof.

7. The nanocapsules according to claim 6, wherein the polyoxyethylene-polyoxypropylene block copolymer(s) comprise at least one of copolymers of formula $EO_x$—$PO_y$-$EO_x$ wherein x ranges from 75 to 85 and y ranges from 25 to 35, copolymers of formula $EO_x$—$PO_y$-$EO_x$ wherein x ranges from 55 to 65 and y ranges from 35 to 45 and copolymers of formula $EO_x$—$PO_y$-$EO_x$ wherein x ranges from 112 to 123 and y ranges from 40 to 50.

8. The nanocapsules according to claim 6, wherein the fatty acids and sucrose esters comprise at least one of stearates and palmitates.

9. The nanocapsules according to claim 1, wherein said polymer comprises at least one of chitosan, alginate, pectin, starch, cellulose, casein and combinations thereof.

10. The nanocapsules according to claim 1, wherein the content of said active ingredient is of at least 5% by mass relative to the dry mass of the nanocapsules.

11. The nanocapsules according to claim 1, wherein the content of said nonionic surfactant is of at least 15% by weight relative to the dry mass of the nanocapsules.

12. The nanocapsules according to claim 1, adsorbed on lactose.

13. The nanocapsules according to claim 1, configured to be implemented in animal nutrition.

14. The nanocapsules according to claim 13, configured to be implemented in monogastrics.

* * * * *